United States Patent [19]
Bailey et al.

[11] Patent Number: 5,998,213
[45] Date of Patent: Dec. 7, 1999

[54] C-TERMINAL SEQUENCING OF PEPTIDES WHICH MAY INCLUDE PROLINE

[75] Inventors: Jerome M. Bailey, Sunnyvale; John E. Shively, Arcadia, both of Calif.

[73] Assignee: City of Hope, Duarte, Calif.

[21] Appl. No.: 08/532,667

[22] PCT Filed: Feb. 15, 1994

[86] PCT No.: PCT/US94/01742
§ 371 Date: Nov. 9, 1995
§ 102(e) Date: Nov. 9, 1995

[87] PCT Pub. No.: WO95/22060
PCT Pub. Date: Aug. 17, 1995

Related U.S. Application Data

[63] Continuation-in-part of application No. 08/094,024, Jul. 26, 1993, Pat. No. 5,432,092, which is a continuation-in-part of application No. 07/801,944, Dec. 3, 1991, Pat. No. 5,180,807.

[51] Int. Cl.[6] .................................................. G01N 33/68
[52] U.S. Cl. ............................ 436/89; 530/345; 530/402
[58] Field of Search ............................... 136/89; 530/345, 530/402

[56] References Cited

U.S. PATENT DOCUMENTS 5,254,475  10/1993  Bailey ........................................ 436/89
5,432,092  7/1995  Bailey et al. .............................. 436/89

FOREIGN PATENT DOCUMENTS 0537981  4/1993  European Pat. Off. .

OTHER PUBLICATIONS

Bailey et al., Protein Science:1(12), pp. 1622–1633 (1992).
Boyd et al., Analytical Biochemistry, 206, pp. 344–352 (1992).

*Primary Examiner*—Lyle A. Alexander
*Attorney, Agent, or Firm*—Rothwell, Figg, Ernst & Kurz, p.c.

[57] ABSTRACT

A carboxy terminal protein sequencing process is disclosed which utilizes diphenyl phosphoroisothiocyanatidate and a heterocyclic amine to produce a thiohydantoin derivative of the C-terminal amino acid. The derivative is readily cleaved. The method is useful to sequence through all of the 20 naturally occuring amino acids.

6 Claims, 16 Drawing Sheets

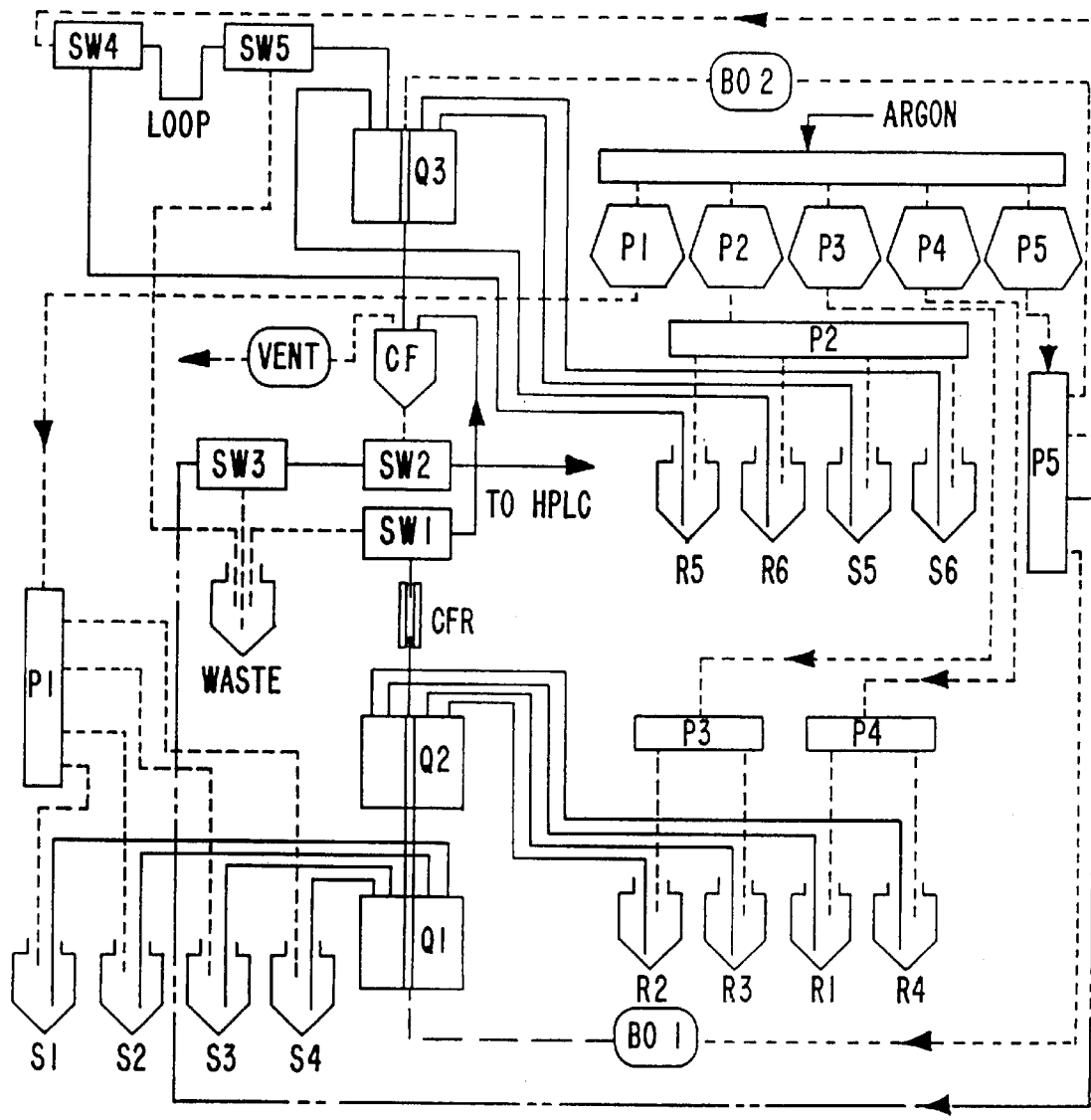
P – PRESSURE VALVE
BO – BLOW OUT VALVE
SW – SWITCHING VALVE
CFR – CONTINUOUS FLOW REACTOR
CF – CONVERSION FLASK
Q – QUAD VALVE
TUBING I.D.
—··— 0.2mm
— — 0.3mm
——— 0.5mm
---- 0.8mm
═══ 1.0mm
 REAGENT, SOLVENT, OR WASTE BOTTLE
F I G. 1

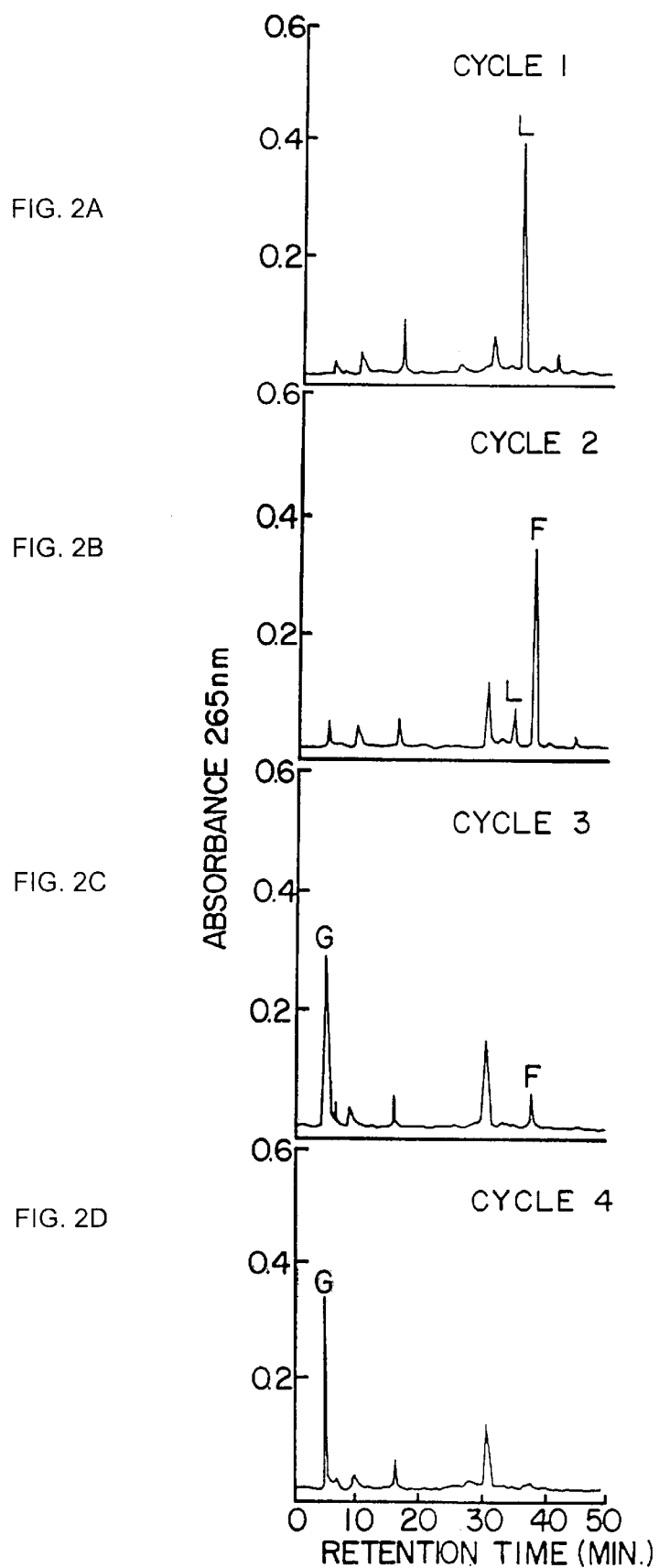

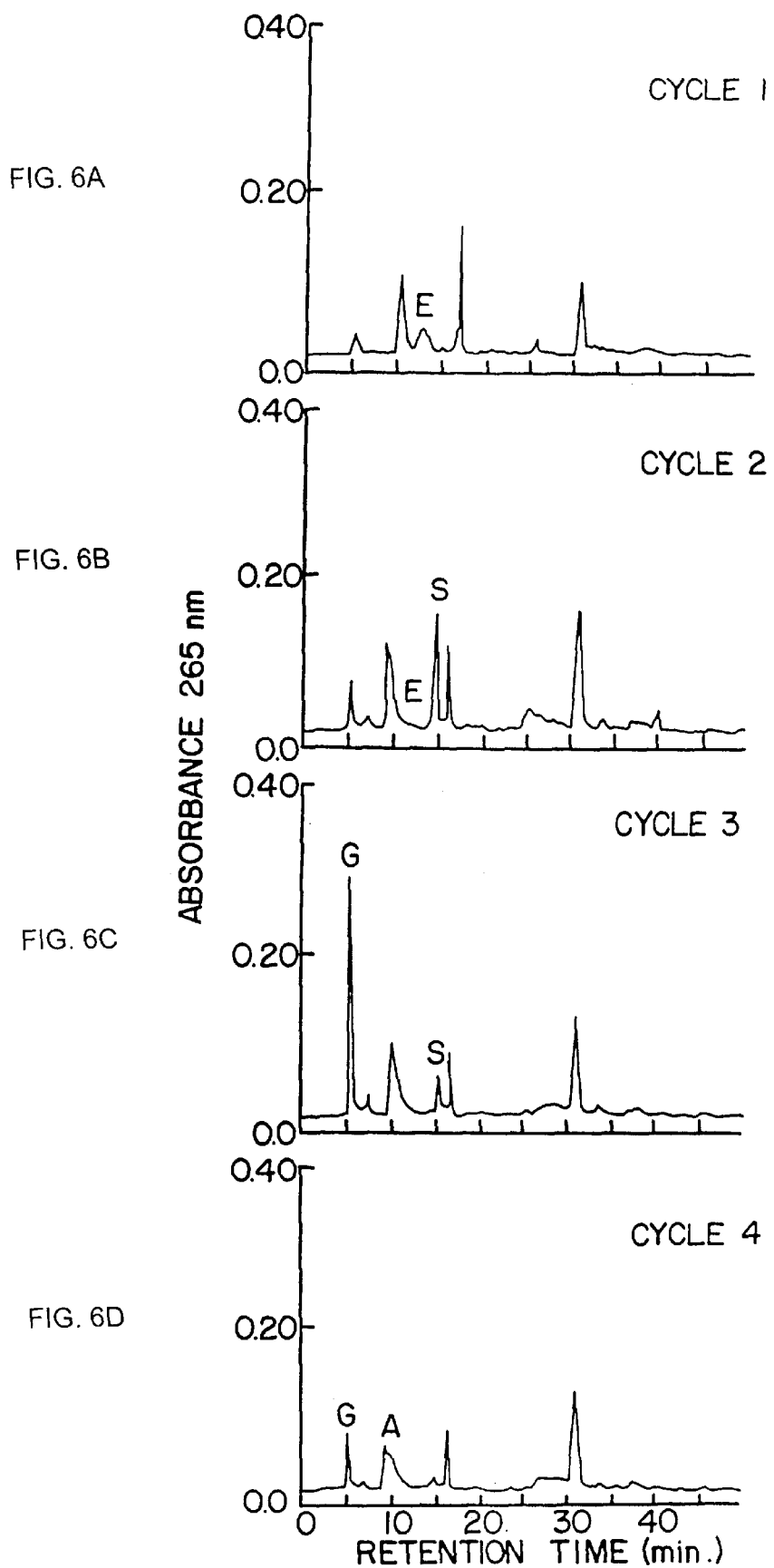

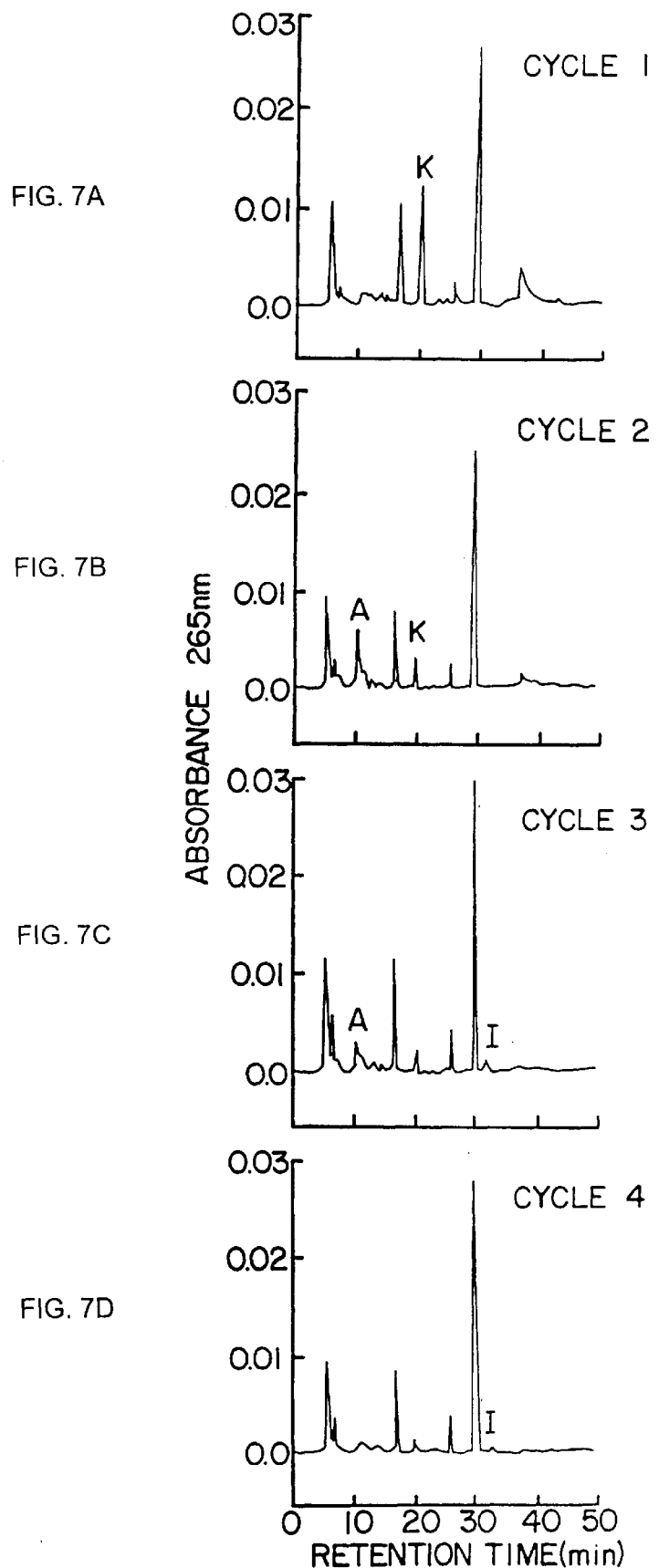

C-TERMINAL SEQUENCING OF PEPTIDES WHICH MAY INCLUDE PROLINE

This application is the national stage of PCT/US 94/01742, filed Feb. 15, 1994, and a continuation-in-part of application Ser. No. 08/094,024 filed Jul. 26, 1993, now U.S. Pat. No. 5,432,092 which is a continuation-in-part of application Ser. No. 07/801,944 filed Dec. 3, 1991, now U.S. Pat. No. 5,180,807.

FIELD OF THE INVENTION

This invention relates to a method for the degradation from the C-terminus of peptides which may include a proline residue.

BACKGROUND OF THE INVENTION

Kenner, et al. *J. Chem. Soc.* 673–678 (1953) describes a C-terminal degradation experiment which required 110 hours to quantitatively form a thiohydantoin amino acid. Bailey U.S. Pat. No. 5,180,807 describes an improvement in which diphenyl phosphoroisothiocyanatidate is used concurrently with a heterocyclic amine, such as pyridine.

Application Ser. No. 08/094,024 illustrates sequential use of diphenyl phosphoroisothiocyanatidate and a heterocyclic amine for C-terminal peptide degradation. In a first step, the peptide which is preferably bound to a solid phase is converted to a carboxylate salt by triethylamine or similar base. In a second step, the carboxylate is reacted with diphenyl phosphoroisothiocyanatidate. In a third step, a heterocyclic amine such as pyridine is added.

SUMMARY OF THE INVENTION

This invention provides a method for the C-terminal degradation of peptides which may include a proline residue. The method of the invention entails (1) formation of a carboxylate on the C-terminal amino acid of the peptide to be sequenced, (2) reaction of the carboxylated peptide with diphenyl phosphoroisothiocyanatidate and a heterocyclic amine to produce a thiohydantoin derivative, (3) protonating the thiohydantoin derivative, and (4) cleaving the protonated thiohydantoin derivative to produce a shortened peptide and a thiohydantoin derivative of the C-terminal amino acid of the peptide to be sequenced.

The polypeptides to be sequenced are preferably either non-covalently applied to the porous tetrafluoroethylene (Zitex) or covalently attached to carboxylated polyethylene (PE—COOH). See application Ser. No. 07/576,943 and U.S. Pat. No. 5,180,807.

DESCRIPTION OF THE FIGURES

FIG. 1 is a schematic of one C-terminal sequencer useful in the practice of the invention.

FIG. 2 illustrates the practice of the invention to sequence YGGFL covalently coupled to carboxylic acid modified polyethylene (PE—COOH). R4 is gas phase pyridine.

FIG. 6 illustrates the practice of the invention to sequence AGSE covalently coupled to PE—COOH.

FIG. 7 illustrates the practice of the invention to sequence Superoxide Dismutase non-covalently coupled to polytetrafluoroethylene (Zitex).

DETAILED DESCRIPTION OF THE INVENTION

Figure 3A:
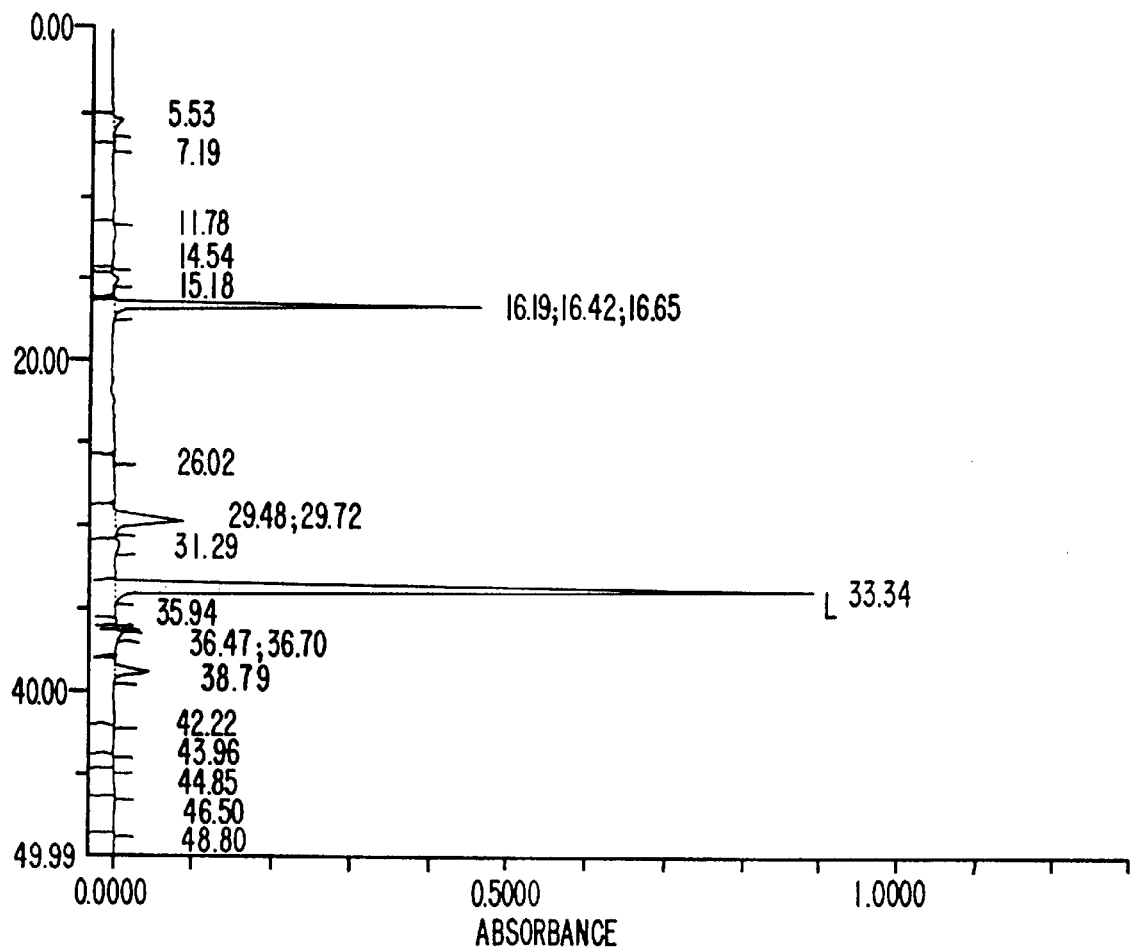
FIGS. 3A–3C illustrates the practice of the invention to sequence YGGFL covalently coupled to PE—COOH. R4 is a solution of tetrazole in dimethylformamide.

The invention provides a preferably sequential four-step method for degradation of a peptide which may include proline.

Step 1. Carboxylation of the Peptide

A carboxylate is formed at the C-terminus of the peptide to be sequenced by reaction with an organic or inorganic base. The specific base utilized is not critical. The carboxylation is preferably carried out by reaction of the peptide to be sequenced with a solution of the selected base in an appropriate solvent. Tertiary trialkyl amines are preferred. Primary and secondary alkyl amines may also be utilized. Alkali metal bases such as sodium or potassium hydroxide are effective and may be utilized in an aqueous solution. Sodium trimethylsilanolate in methyl alcohol solution is appropriate.

When utilized in aqueous solution, alkyl amines such as triethylamine are preferably present in a concentration of about 5% by volume. When such amines are utilized in an organic solvent solution, a concentration of about 40% to 60% by volume is appropriate. The selection of an appropriate concentration of base in the solvent utilized is within the skill of the art. The preferred carboxylation reagent for use in the practice of this invention is a solution containing 40% to 60% by volume of triethylamine in an anhydrous methanol. The carboxylation reaction is appropriately conducted at a temperature from 30° to 70° C.

Step 2. Formation of the Thiohydantoin Derivative of the Peptide to be Sequenced The peptide carboxylate formed in step 1 is converted to a thiohydantoin by reaction with diphenyl phosphoroisothiocyanatidate and with an aromatic heterocyclic ring containing nitrogen. Sequential reaction, first with diphenyl phosphoroisothiocyanatidate and then with an aromatic heterocyclic ring containing nitrogen, permits sequencing through Asp and Glu. The diphenyl phosphoroisothiocyanatidate and amine reagents are utilized in organic solvents such as acetonitrile, dimethylformamide, ethyl acetate, benzene and toluene. The concentration of the diphenyl phosphoroisothiocyanatidate in the solvent is preferably from 2% to 70% by volume. The reactions whether simultaneous or sequential are conducted at a temperature from 15° C. to 90° C., preferably 50° C. to 70° C.

The amine reagent rapidly promotes removal of the phosphoryl moiety from the phosphoroisothiocyanatidate reaction product. The invention includes the use of any aromatic heterocyclic compound in which nitrogen is present in the ring. Amines useful in the invention include, but are not limited to, pyridine, derivatized pyridines such as dimethylaminopyridine, pyridazine, pyrimidine, pyrazine, triazine, pyrrole, pyrazole, imidazole, triazole, or tetrazole. Pyridine is preferred and may be used either per se, e.g., in the gas phase, or in an organic solvent medium such as acetonitrile or dimethylformamide at any concentration in excess of 0.1% by volume.

Step 3. Protonation of the Thiohydantoin

Protonation of the thiohydantoin product of Step 2 may be accomplished with any of a number of acids. Trifluoromethanesulfonic acid and trifluoroacetic acid are preferred. Acids found to be useful include hydrochloric, acetic and formic. The protonation reaction is appropriately conducted at a temperature of from about 30° C. to 90° C., preferably 50° C.

Step 4. Cleavage of the C-terminal Thiohydantoin

A unique feature of this invention is the efficiency with which the protonated thiohydantoin derivative is cleaved to provide a shortened peptide and a thiohydantoin derivative of the C-terminal amino acid.

Cleavage is best achieved by reaction with the sodium trimethylsilanolate. The sodium trimethylsilanolate is utilized as a 0.01M to 1.0M, preferably 0.1M solution in an alcohol. A preferred solvent contains equal parts of methanol and t-butanol. See PCT application U.S. Ser. No. 90/02723.

Other salts of the trimethylsilanolate ion, such as those having the monovalent cations $K^+$, $Li^+$, $Rb^+$, and $Cs^+$ may be utilized. The trimethyl group may be replaced with other alkyl groups or with phenyl groups.

When the C-terminal derivative is thiohydantoin proline, the preferred cleavage reagent is gas phase water (water vapor) at a temperature of 30° C. to 70° C., preferably 50° C. The thiohydantoin derivative of the C-terminal amino acid residue is analyzed by reverse phase HPLC. The free carboxylate is regenerated, for example, by a second treatment with sodium trimethylsilanolate.

Covalent Coupling of Peptides to Carboxylic Acid Modified Polyethylene Film

Samples of PE—COOH film were treated with an 1N solution of HCl for 1–2 minutes at room temperature, in order to convert the surface carboxylic acid groups to the free acid form, prior to the covalent attachment of peptide samples.

The strips of PE—COOH film (1×12.5 mm) were then activated by an excess of DCC (dicyclohexylcarbodiimide) in anhydrous DMF (1 g/1 ml) for 1 hour at room temperature. At the end of the activation reaction, the excess reagent was removed by rinsing the strips with anhydrous DMF. Each activated PE—COOH strip was inserted into a continuous flow reactor (CFR) (Shively et al., 1987) containing a solution of leucine enkephalin (YGGFL) in 50% aqueous DMF overnight at 22° C. The microbore tubing on one end of the CFR was sealed by heating and then pinched closed with pliers. After the coupling reaction, the support was rinsed with coupling solvent and acetonitrile, and then dried in a vacuum centrifuge.

Description of FIG. 1 Sequencer and Program

Below is described the instrument and detailed description of the program used for the C-terminal sequencing of C-terminal proline containing polypeptides. This program can be used for the other 19 amino acids as well. It is therefore applicable to all of the common amino acids found in proteins.

The overall design of the sequencer shown by FIG. 1 is similar in some respects to the gas phase sequencer described by Calaycay et al., *Anal.Biochem.* 192:23–31 (1991).

The reagent and solvent bottles associated with the instrument depicted in FIG. 1 are shown. Four reagent bottles, R2–R5, and five solvent bottles, S1–S5, are utilized in the practice of the invention illustrated by the ensuing examples. Reagents from bottles R2–R4 and solvents from bottles S1–S4 are delivered to the continuous flow reactor (CFR). Reagent from bottle R5 and solvent from bottle S5 are delivered to the conversion flask (CF). In N-terminal sequencing, the CF serves to convert the ATZ derivative of the cleaved amino acid into a PTH (phenylthiohydantoin) just before analysis by HPLC. In C-terminal sequencing, the CF serves as a place to hold the cleaved thiohydantoin amino acid just prior to injection into the HPLC. The composition of the reagents and solvents is set forth in Table I.

TABLE I

| COMPOSITION OF REAGENTS AND SOLVENTS FOR PROLINE PEPTIDES | |
|---|---|
| R1 | — |
| R2 | Diphenyl phosphoroisothiocyanatidate in acetonitrile (3.0M) |
| R3 | 0.10M sodium trimethylsilanolate in 50% methanol, 50% t-butyl alcohol |
| R4 | Pyridine (delivered in the gas phase) |
| R5 | 2.0% trifluoroacetic acid in water |
| S1 | Water (delivered in the gas phase) |
| S2 | Methanol |
| S3 | 25% acetonitrile, 75% ethyl acetate |
| S4 | Trifluoromethanesulfonic acid (delivered in the gas phase) |
| S5 | Methanol |
| S6 | — |

To deliver the reagents and solvents to the CFR, a gentle pressure (1.5 atms) of argon is applied to each bottle. Argon was chosen because of its chemical inertness. Other suitable inert gases could be helium and nitrogen. There are a total of five pressure regulators (P1–P5). P1 is for S1–S4, P2 is for S5, S6, R5, S6, P3 is for R2 and R3, P4 is for R1 and R4, and P5 is for blow out functions and argon delivery functions (drying, etc.). When it is time to deliver a reagent (for example R1), a solenoid actuated valve on P4 is opened in order to let the argon pass through the valve to the bottle (R1). Since each bottle is sealed, the argon pressure pushes the solvent through the line at the bottom to the valve block (in this case Q2). There is a solenoid actuated valve on Q2, and a valve on SW1 (for venting) is opened to allow the solvent flow into the valve block, Q2 and on into the CFR. Once the CFR is full, the flow is stopped by closing the valves and the reaction is allowed to continue for the desired length of time. After the reaction, the Angar valve (BO1) and SW1 (to waste) is opened to allow argon to pass through the valve blocks Q1 and Q2. This pushes the reagent or solvent in the CFR out to waste or to the CF, depending on which solenoid is actuated on the three-way switching valve just after the CFR. The program for sequencing therefore consists of only opening and closing solenoid actuated valves at various times.

The program for C-terminal sequencing utilizing the sequencer depicted in FIG. 1 is set forth in Tables II and III.

TABLE II

C-TERMINAL SEQUENCER INITIAL PROGRAM FOR PROLINE PEPTIDES

| Continuous Flow Reactor (55° C.) | Conversion Flask (45° C.) | Duration (sec) |
|---|---|---|
| pressurize S4 | | 3 |
| deliver S4 | | 60 |
| pressurize S1 | | 3 |
| deliver S1 | | 60 |
| pressurize S4 | | 3 |
| deliver S4 | | 60 |
| pressurize S1 | | 3 |
| deliver S1 | | 60 |
| blow out S1 | | 60 |
| pressurize S3 | | 3 |
| deliver S3 | | 30 |
| blow out S3 | | 45 |
| pressurize R3 | | 3 |
| deliver R3 | | 4 |
| R3 reaction | | 120 |
| blow out R3 | | 20 |
| pressurize R3 | | 3 |
| deliver R3 | | 4 |
| R3 reaction | | 120 |
| blow out R3 | | 60 |

TABLE III

C-TERMINAL SEQUENCER PROGRAM SUMMARY FOR PROLINE PEPTIDES

| Continuous Flow Reactor (55° C.) | Conversion Flask (45° C.) | Duration[a] (sec) |
|---|---|---|
| R2 reaction | | 3, 2, 120, 15 |
| S3 rinse | | 3, 2, —, 30 |
| R4 reaction | | 3, 60, —, 30 |
| S3 rinse | | 3, 5, —, 60 |
| R2 reaction | | 3, 2, 120, 15 |
| S3 rinse | | 3, 2, —, 30 |
| R4 reaction | | 3, 60, —, 30 |
| S3 rinse | | 3, 5, —, 60 |
| R2 reaction | | 3, 2, 120, 15 |
| S3 rinse | | 3, 2, —, 30 |
| R4 reaction | | 3, 60, —, 30 |
| S3 rinse | | 3, 60, —, 10 |
| S3 rinse | | 3, 60, —, 10 |
| S3 rinse | | 3, 60, —, 10 |
| S3 rinse | | 3, 60, —, 20 |
| S4 reaction | | 3, 10, —, — |
| S1 reaction | | 1, 20, —, — |
| S4 reaction | | 3, 120, —, — |
| S4 reaction | | 3, 180, —, 60 |
| S2 rinse | | 3, 1.5, —, — |
| S2 to CF | | 40 |
| S3 rinse | | 3, 30, —, 20 |
| S2 rinse | | 3, 60, —, 10 |
| S3 rinse | | 3, 60, —, 20 |
| S2 rinse | | 3, 60, —, 60 |
| Raise Temp. to 60° C. | | |
| R3 reaction | | 3, 2, 180 |
| R3 to CF | | 40 |
| Temp. back to 50° C. | Dry in CF | 600 |
| | R5 pressurize | 3 |
| | R5 delivery to loop | 4 |
| | Loop to CF | 8 |
| | R5 pressurize | 3 |
| | R5 delivery to loop | 4 |
| | Loop to CF | 8 |
| | CF vent | 3 |
| | CF to HPLC | 15 |
| pause | pause | 60 |
| R3 pressurize | | 3, 2, —, — |
| pause | | 5 |
| R3 to CF | | 20 |
| | pause | 5 |
| | CF to waste | 40 |
| | pressurize S5 | 3 |
| | deliver S5 | 1.5 |
| Dry | Empty CF | 120 |

[a] The first time is pressure, the second delivery, the third reaction time, and the fourth blowout.

The steps in the initial program described in Table II are performed only once for a particular sample and are only performed at the beginning of a sequencing experiment. The "pressurize S4" step means that the S4 bottle is allowed to pressurize with argon for 30 seconds.

The second step, "Deliver S4", the valve on P1 which corresponds to S4 is still open to maintain pressure on S4, but the solenoid on the reagent block (Q2) for S4 is also opened, permitting S4 vapor to flow into the CFR. Additionally, the solenoid on the three-way switching valve (SW1) is opened in order to permit equalization of pressure in the closed system and to allow any overflow to go to a waste bottle. This flow is maintained for sixty seconds. At the end of sixty seconds, all of the solenoid actuated valves are closed and the S4 reagent, in this case trifluoromethanesulfonic acid, is then blown out of the CFR to the waste bottle by actuated valve BO1 and the waste valve (SW1). This permits argon to push the contents of the CFR to waste. The same procedure, by actuation of the appropriate solenoids, is repeated for the remaining steps in the program. The purpose of this program is to convert the C-terminal carboxylic acid group to a carboxylate.

Table III describes the sequence of events which will derivatize the C-terminal amino acid to a thiohydantoin and specifically cleave it to leave a shortened polypeptide ready for continued sequencing. The sequence of four events which, as illustrated, entails treatment of the polypeptide sample with diphenyl phosphoroisothiocyanatidate (R2), rinsing with ethyl acetate/acetonitrile (S3), treatment with gas phase pyridine (R4), and rinsing with ethyl acetate/acetonitrile (S3), is repeated three times in order to complete derivatization of the C-terminal amino acid.

At this stage, 90% or greater of the polypeptide C-terminal amino acid is derivatized to a thiohydantoin, except in the case of proline. The sample is then extensively washed with ethyl acetate/acetonitrile (S3) in order to remove any remaining isothiocyanate reagent and pyridine present in the CFR or in various lines that add UV absorbing impurities to the HPLC chromatogram of the related thiohydantoin amino acid. The sample is then treated with gas phase trifluoromethanesulfonic acid (S4) in order to protonate the thiohydantoin ring formed in the case when the C-terminal amino acid is proline. This treatment is then followed by reaction with vapor phase water (S1) to specifically hydrolyze the newly formed thiohydantoin proline. Methanol (S2) is then delivered to the CFR in order to dissolve any thiohydantoin proline formed and carry it to the CF where it is then dried. The acid/water/methanol treatment has no effect on the other 19 commonly occurring amino acids. C-terminal thiohydantoins other than proline are not cleaved by the acid/water treatment and still must be cleaved by treatment with sodium trimethylsilanolate (R3).

Cleavage is accomplished when sodium trimethylsilanolate in methanol and t-butanol (R3) is brought into the CFR, allowed to react for 180 seconds. Then the contents of the CFR are pushed into the CF and combined with the methanol extract described above. Once in the CF, the alcoholic solution containing the thiohydantoin is dried by blowing a stream of argon on it for 600 seconds. This is accomplished by opening valves (SW2 and SW3) under the CF as well as the valve which vents the CF.

EXAMPLE 1

This example describes the sequencing of YGGFL (5.6 nmoles) covalently coupled to carboxylic acid modified polyethylene, for four cycles utilizing a computer automated C-terminal sequencer as depicted by FIG. 1 and the program set forth above in which the R4 reagent is pyridine delivered in the gas phase, with the exception that the S1 and S4 reaction steps are not included.

The product of each cycle is subjected to HPLC. FIG. 2 shows the chromatograms resulting from cycles 1–4. In each case, the derivatized C-terminal amino acid is identified by retention time on a C-18 reverse phase column. The separation of the thiohydantoin amino acids was performed on a 2.1×250 mm Reliasil C-18 column at 35° C. with a flow rate of 0.15 ml/min. Solvent A is 0.1% trifluoroacetic acid in water. Solvent B is 80% acetonitrile, 10% water, and 10% methanol. Gradient elution is performed as follows: 0% B for 2 min., 0–4% B for 35 min., and 35–50% B for 10 min. Absorbance is monitored at 265 nm.

EXAMPLE 2

Figure 3B:
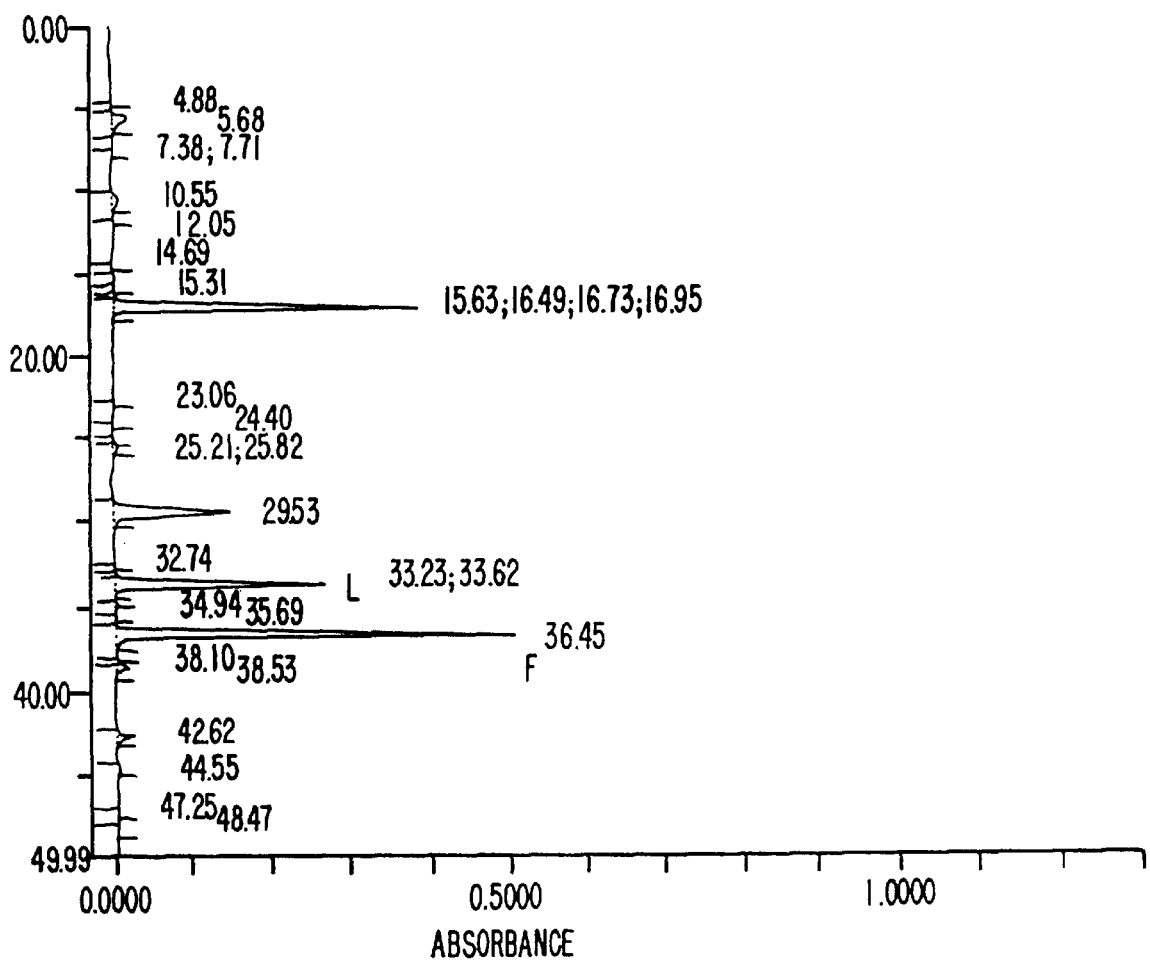
Figure 3C:
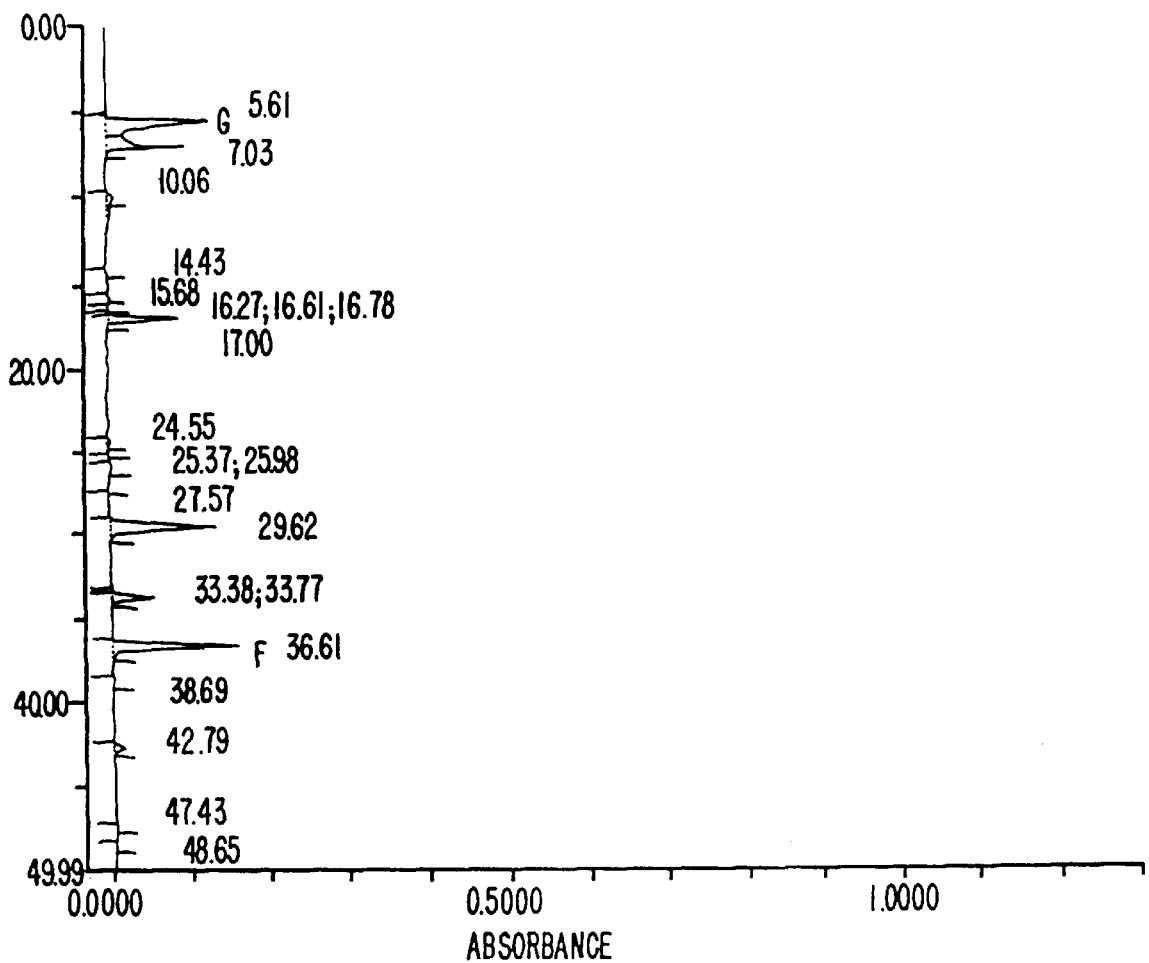
Figure 4A:
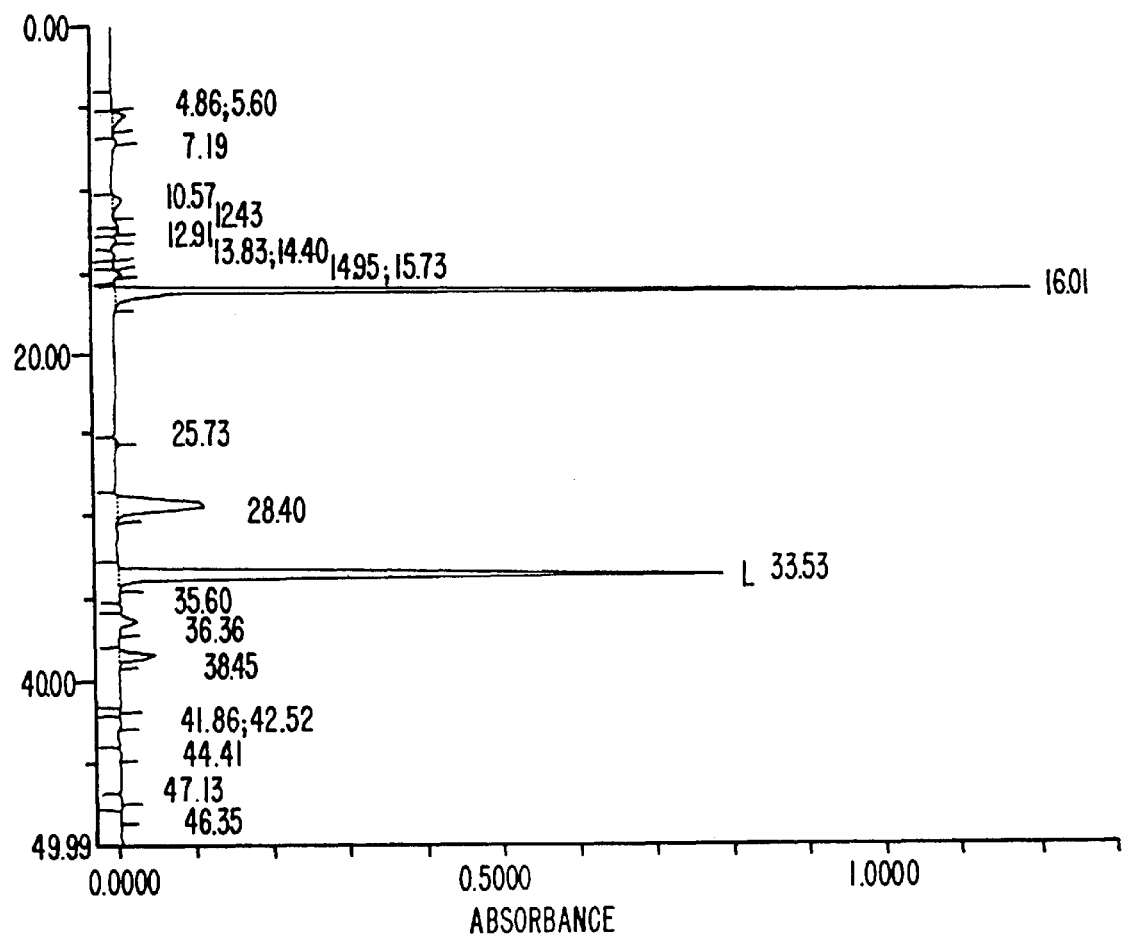
FIGS. 4A to 4F illustrate the practice of the invention to sequence YGGFL covalently coupled to PE—COOH. R4 is a solution of tetrazole in acetonitrile.
Figure 4B:
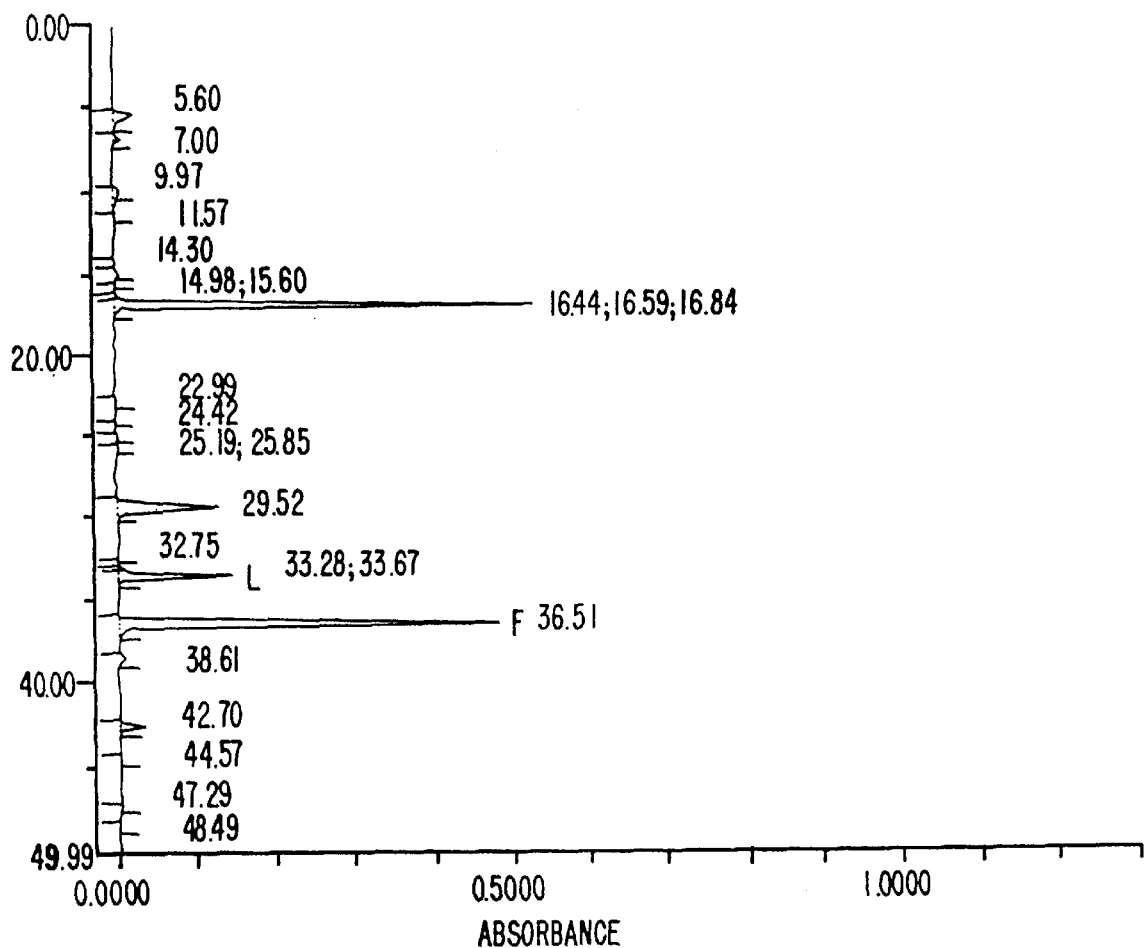
Figure 4C:
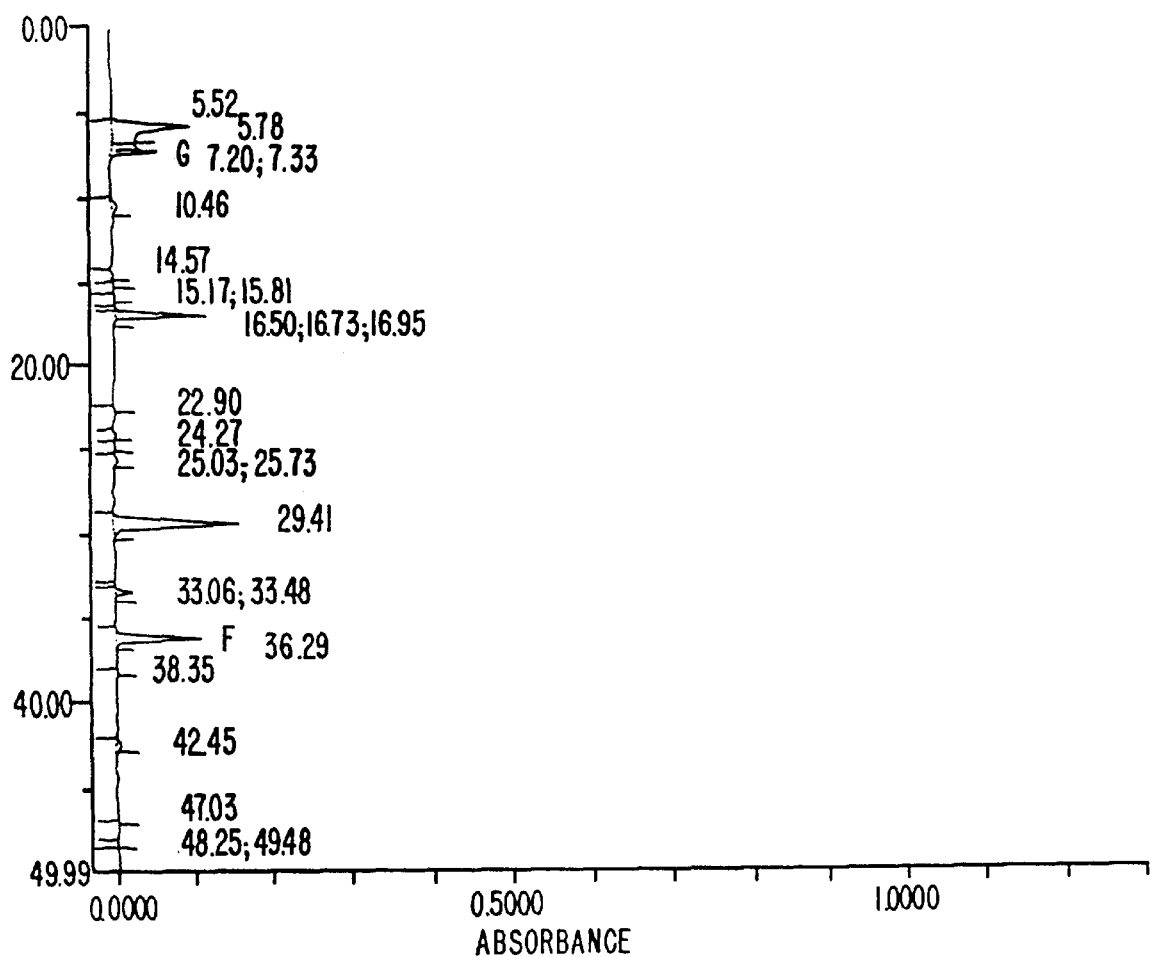
Figure 4D:
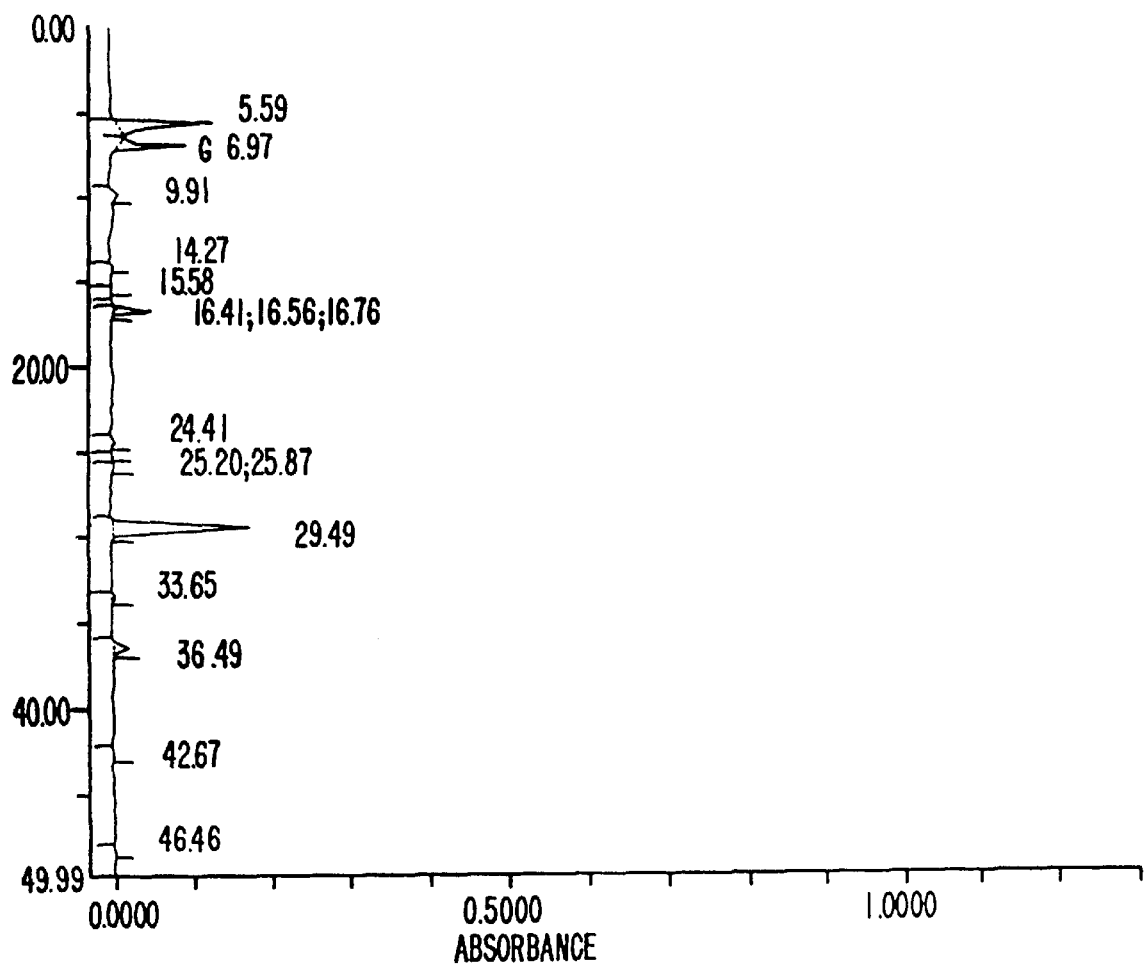
Figure 4E:
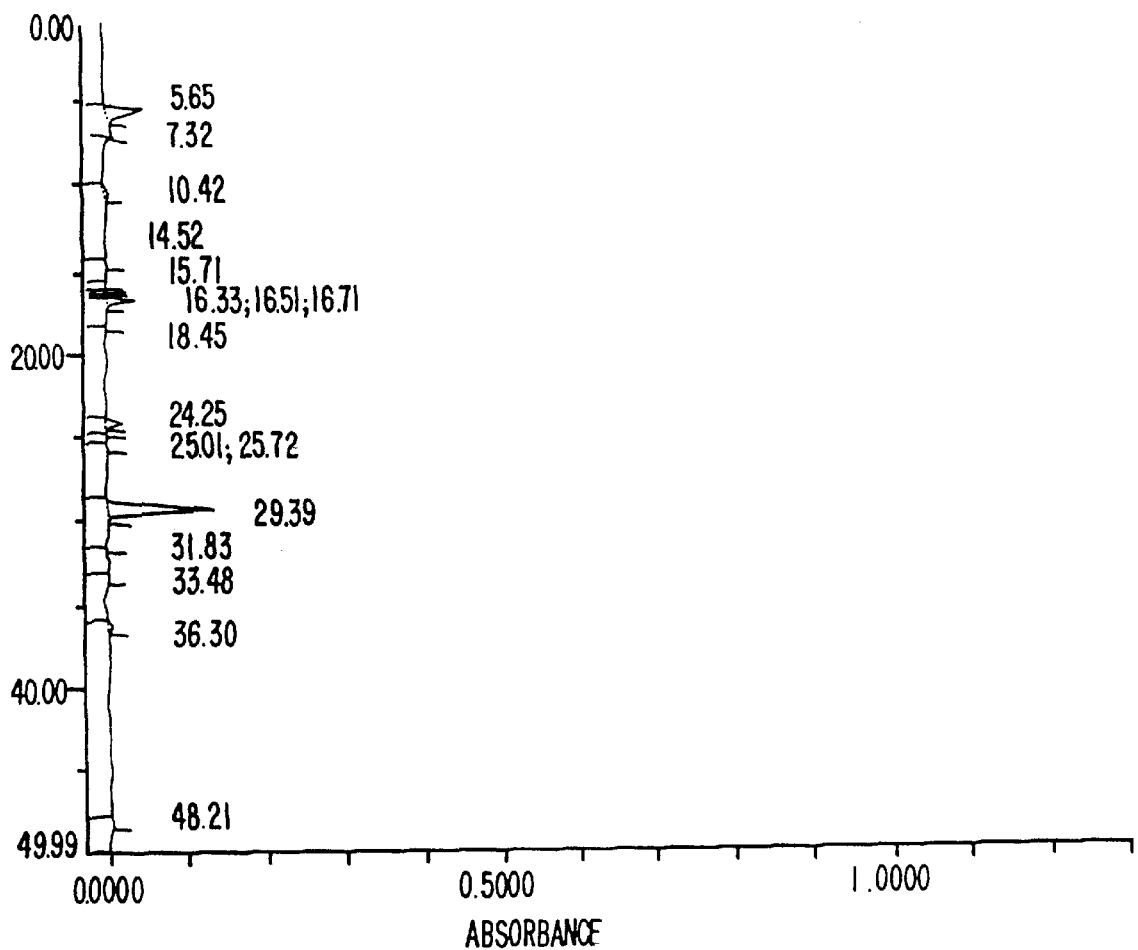
Figure 4F:
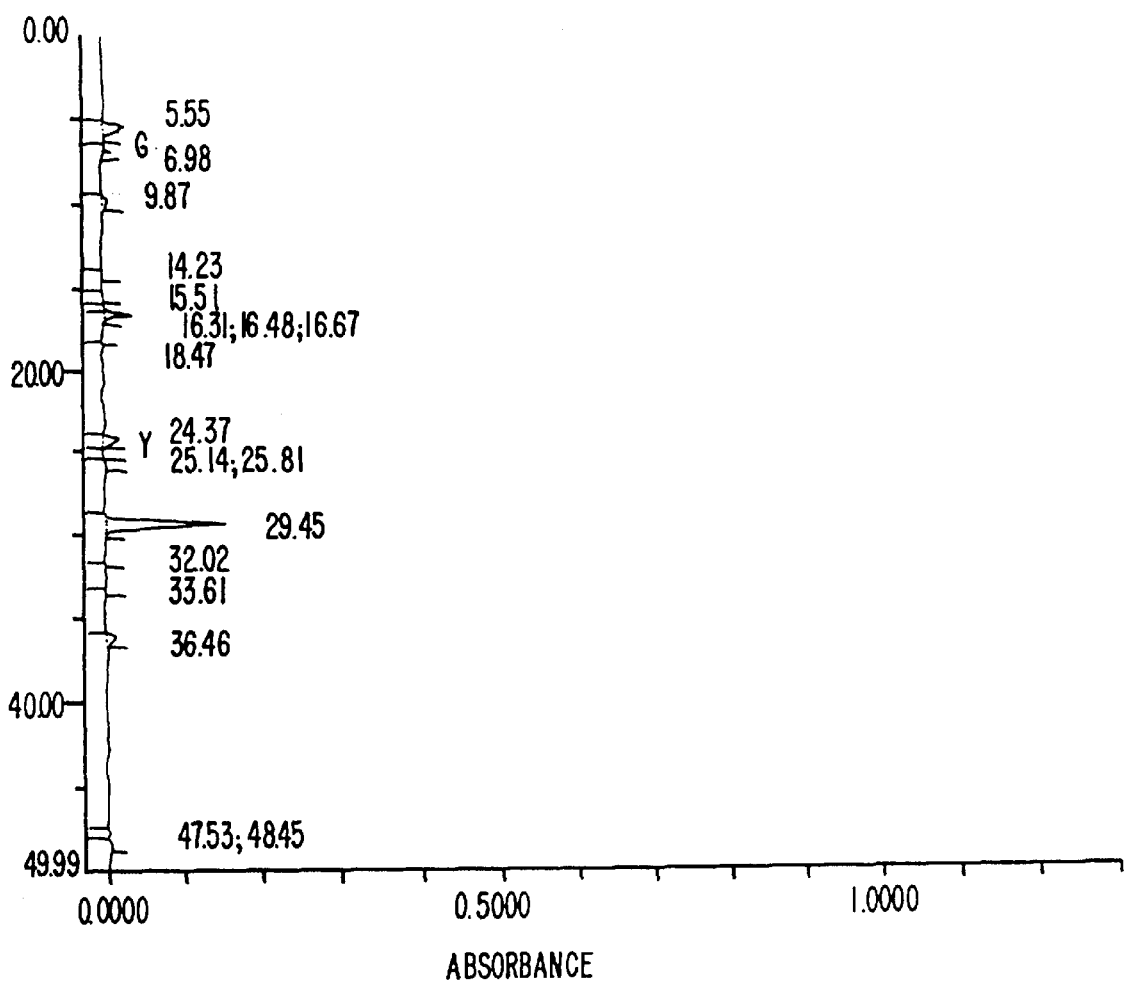

Example 1 is repeated with the exception that R4 is a solution of 0.1 grams tetrazole in 30 milliliters of dimethylformamide. The results are depicted by FIG. 3.

EXAMPLE 3

Example 1 is repeated with the exception that R4 is a solution of 0.1 grams tetrazole in 30 milliliters of acetonitrile. The results are depicted by FIGS. 4A, 4B, 4C, 4D, 4E and 4F.

EXAMPLE 4

This example describes the sequencing of the tripeptide LAP (15 nmoles), covalently coupled to carboxylic acid modified polyethylene, for four cycles utilizing a computer automated C-terminal sequencer as depicted by FIG. 1 and the program set forth above. HPLC separation of the amino acid thiohydantoins is performed as described in Example 1. The R4 reagent is pyridine delivered in the gas phase. The results are depicted by FIG. 5.

EXAMPLE 5

This example describes the sequencing of the tetrapeptide AGSE (9 nmoles), covalently coupled to carboxylic acid modified polyethylene, for four cycles utilizing a computer automated C-terminal sequencer as depicted by FIG. 1 and the program set forth above with the exception that the S1 and S4 reaction steps are not included. HPLC separation of the amino acid thiohydantoins is performed as described in Example 1. The R4 reagent is pyridine delivered in the gas phase. The results are depicted by FIG. 6.

EXAMPLE 6

This example describes the sequencing of the protein Superoxide Dismutase (400 pmoles), non-covalently applied to a Zitex strip (1 mm×10 mm), for four cycles utilizing a computer automated C-terminal sequencer as depicted by FIG. 1 and the program set forth above with the exception that the S1 and S4 reaction steps are not included. HPLC separation of the amino acid thiohydantoins is performed as described in Example 1. The R4 reagent is pyridine delivered in the gas phase. The results are depicted by FIG. 7.

EXAMPLE 7

This example describes the sequencing of the protein Ribonuclease A (4.5 nmoles), non-covalently applied to a Zitex strip (1 mm×10 mm), for four cycles utilizing a computer automated C-terminal sequencer as depicted by FIG. 1 and the program set forth above with the exception that the S1 and S4 reaction steps are not included. HPLC separation of the amino acid thiohydantoins is performed as described in Example 1. The results are depicted by FIG. 8.

EXAMPLE 8

This example describes the sequencing of the protein Hemoglobin α chain (4.1 nmoles), non-covalently applied to a Zitex strip (1 mm×10 mm), for four cycles utilizing a computer automated C-terminal sequencer as depicted by FIG. 1 and the program set forth above with the exception that the S1 and S4 reaction steps are not included. HPLC separation of the amino acid thiohydantoins is performed as described in Example 1. The results are depicted by FIG. 9.

EXAMPLE 9

This examples involves a solution phase experiment in which C-terminal Asp did not derivatize to a thiohydantoin with simultaneous reaction of diphenyl phosphoroisothiocyanatidate and pyridine. Pro-Phe-Asp (60 nmol) N-protected with an acetyl group was reacted with diphenyl phosphoroisothiocyanatidate (0.06 mol) and pyridine (0.12 mmol) in acetonitrile for 40 minutes at 50° C. The total reaction volume was 0.1 ml. At the end of the reaction period, the peptide solution was evaporated to dryness by vacuum centrifugation. The peptide products were re-dissolved in 0.1 ml of 0.1% (v/v) trifluoroacetic acid in water and analyzed by reverse phase HPLC as described in Bailey et al., *Biochem.* 29:3145–3156 (1990). A single peptide product was found. The mass of this peptide, obtained by FAB/MS, was found to be equivalent to the starting peptide, N-acetyl-Pro-Phe-Asp (MH$^+$=420).

We claim:

1. In a method for the C-terminal degradation of a peptide in which the C-terminal amino acid is proline and in which a thiohydantoin derivative of said C-terminal proline is formed by reaction with diphenyl phosphoroisothiocyanatidate and a heterocyclic compound having a ring containing nitrogen, the improvement which comprises, first, protonation of said derivative; second, cleavage of said derivative by reaction with water to provide a shortened peptide and thiohydantoin proline.

2. A method as defined by claim 1 in which said derivative is protonated by trifluoromethanesulfonic acid or trifluoroacetic acid at a temperature of 30° C. to 90° C.

3. A method as defined by claim 1 in which said water is gas or liquid phase water and cleavage is conducted at a temperature of 30° C. to 90° C.

4. A method for degrading a peptide from the C-terminus which comprises the following steps:
   (i) forming a carboxylate of the C-terminal amino acid residue of said peptide, (ii) reacting said carboxylate with a combination of diphenyl phosphoroisothiocyanatidate and an aromatic heterocyclic amine to provide a thiohydantoin derivative of the carboxylated peptide of step (i), (iii) protonating said thiohydantoin derivative, and (iv) cleaving said protonated derivative to provide a shortened peptide and a thiohydantoin derivative of the amino acid residue at the C-terminus of said peptide to be sequenced.

5. A method as defined by claim 4 in which (i) the carboxylate is formed in step (i) by reaction of said peptide with a 1% to 20% aqueous solution of triethylamine or with 1% to 20% solution of triethylamine in methanol, (ii) step (ii) is conducted by sequential reaction of said carboxylate first with diphenyl phosphoroisothiocyanatidate and thereafter with an aromatic heterocyclic compound having nitrogen in the ring, (iii) protonation step (iii) is accomplished by reacting the product of step (ii) with trifluoromethane sulfonic acid or trifluoroacetic acid, and (iv) cleavage step (iv) is accomplished by reaction of the product of step (iii) with water vapor at a temperature of 50° C. to 70° C. in the case of C-terminal proline or with sodium trimethylsilanolate in the case when the C-terminal amino acid is other than proline.

6. A method for the C-terminal degradation of a peptide including a proline, Asp or Glu residue which comprises:

(i) providing a C-terminal carboxylate of said peptide, (ii) reacting said carboxylate simultaneously or sequentially with a diphenyl phosphoroisothiocyanaditate or an aromatic heterocyclic amine to form a thiohydantoin derivative thereof, (iii) protonating said thiohydantoin derivative, and (iv) cleaving said protonated derivative to provide a shortened peptide and a thiohydantoin derivative of the amine and residue at the C-terminus of said peptide, wherein (v) said step (ii) is accomplished by sequential reaction, first, with diphenyl phosphoroisothiocyanatidate and, thereafter, with an aromatic heterocyclic amine when said carboxylate is a carboxylate of Asp or Glu, (vi) said cleaving step (iv) is accomplished by reaction with water when said protonated thiohydantoin derivative is protonated thiohydantoin proline and wherein (vii) said step (iv) is accomplished by reaction with sodium trimethylsilanolate when said protonated thiohydantoin derivative is other than proline.

* * * * *

UNITED STATES PATENT AND TRADEMARK OFFICE
CERTIFICATE OF CORRECTION

PATENT NO. : 5,998,213
DATED : December 7, 1999
INVENTOR(S) : Bailey et al.

It is certified that error appears in the above-identified patent and that said Letters Patent is hereby corrected as shown below:

In the Abstract
In the Abstract "occuring" should be --occurring--.

Figure 5A:
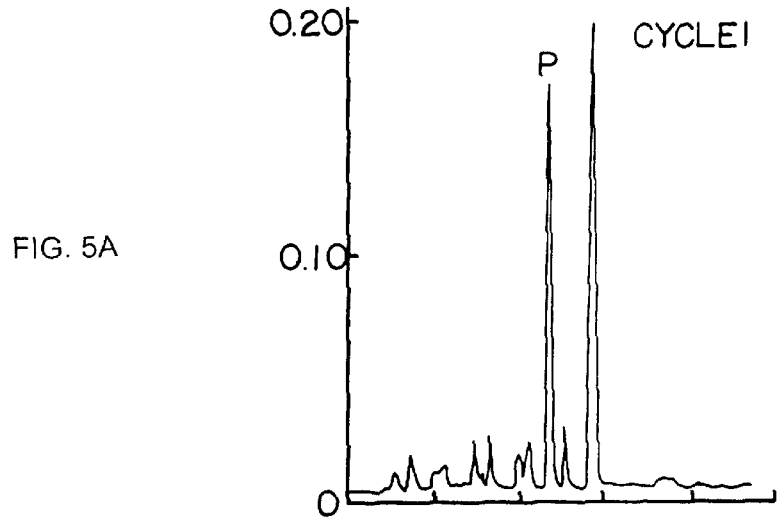
FIG. 5 illustrates the practice of the invention to sequence LAP covalently coupled to PE—COOH.
Figure 5B:
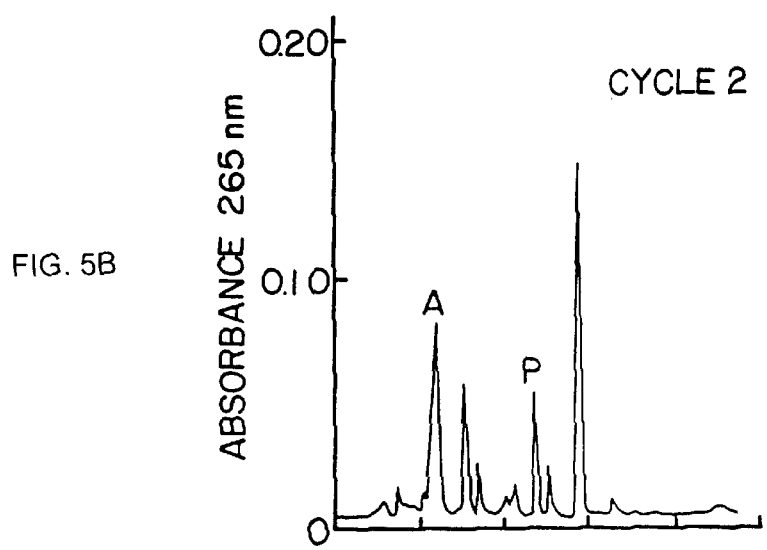
Figure 5C:
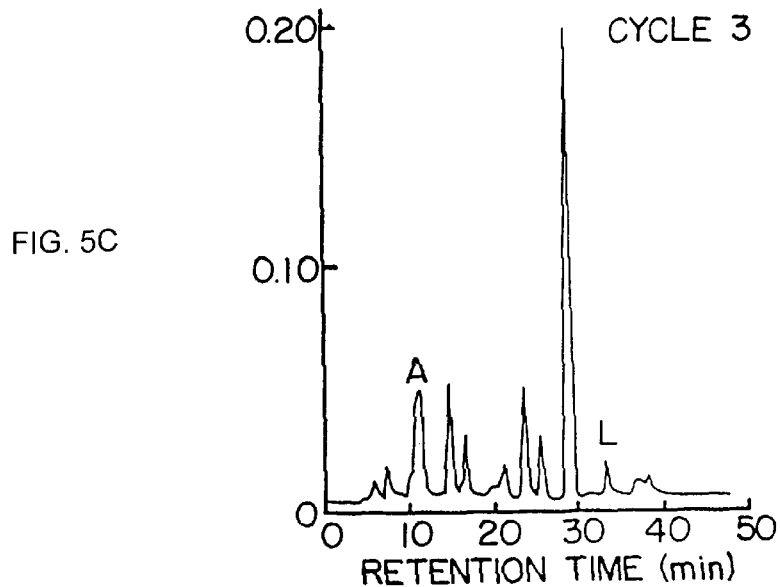
Figure 8A:
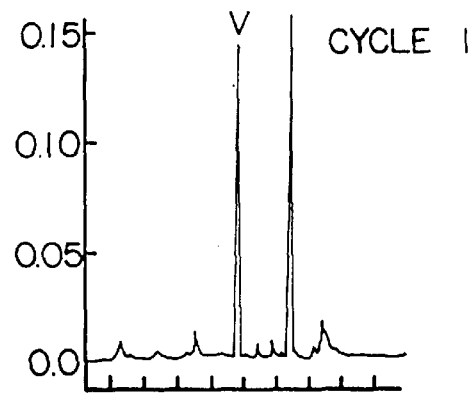
FIG. 8 illustrates the practice of the invention to sequence Ribonuclease A non-covalently coupled to polytetrafluoroethylene (Zitex).
Figure 8B:
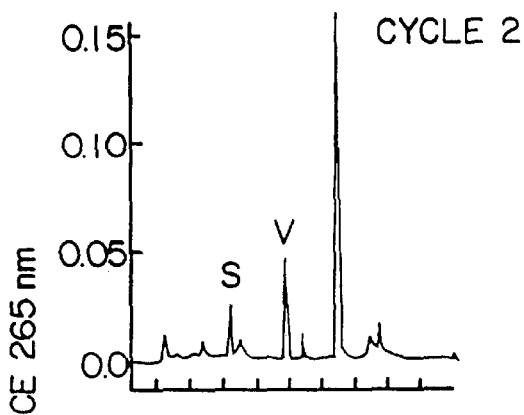
Figure 8C:
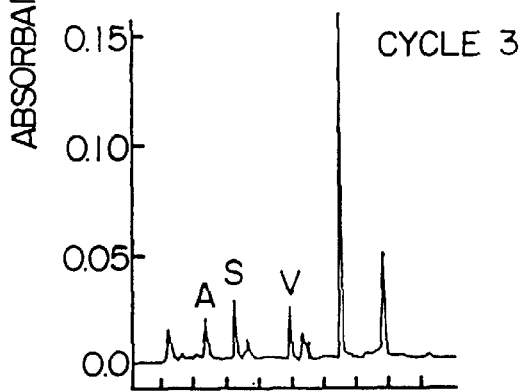
Figure 8D:
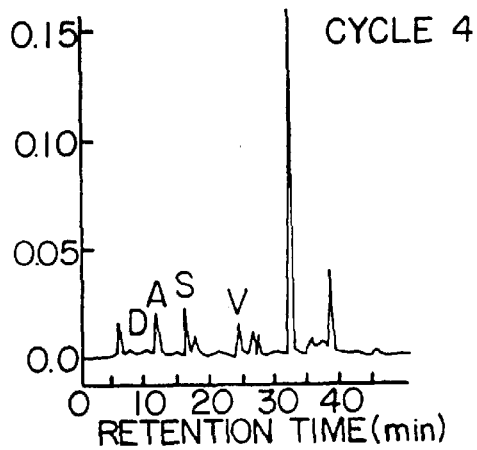

In the Specification:
Column 1,
Line 54, delete "FIG. 2 illustrates" insert --FIGS. 2A-2D illustrate--.
Line 58, "illustrates" should be --illustrate--.
Line 64, delete "FIG. 5 illustrates" insert --FIGS. 5A-5D illustrate--.
Line 66, delete "FIG. 6 illustrates" insert --FIGS 6A-6D illustrate--.

Figures 9A, 9B, 9C, 9D:
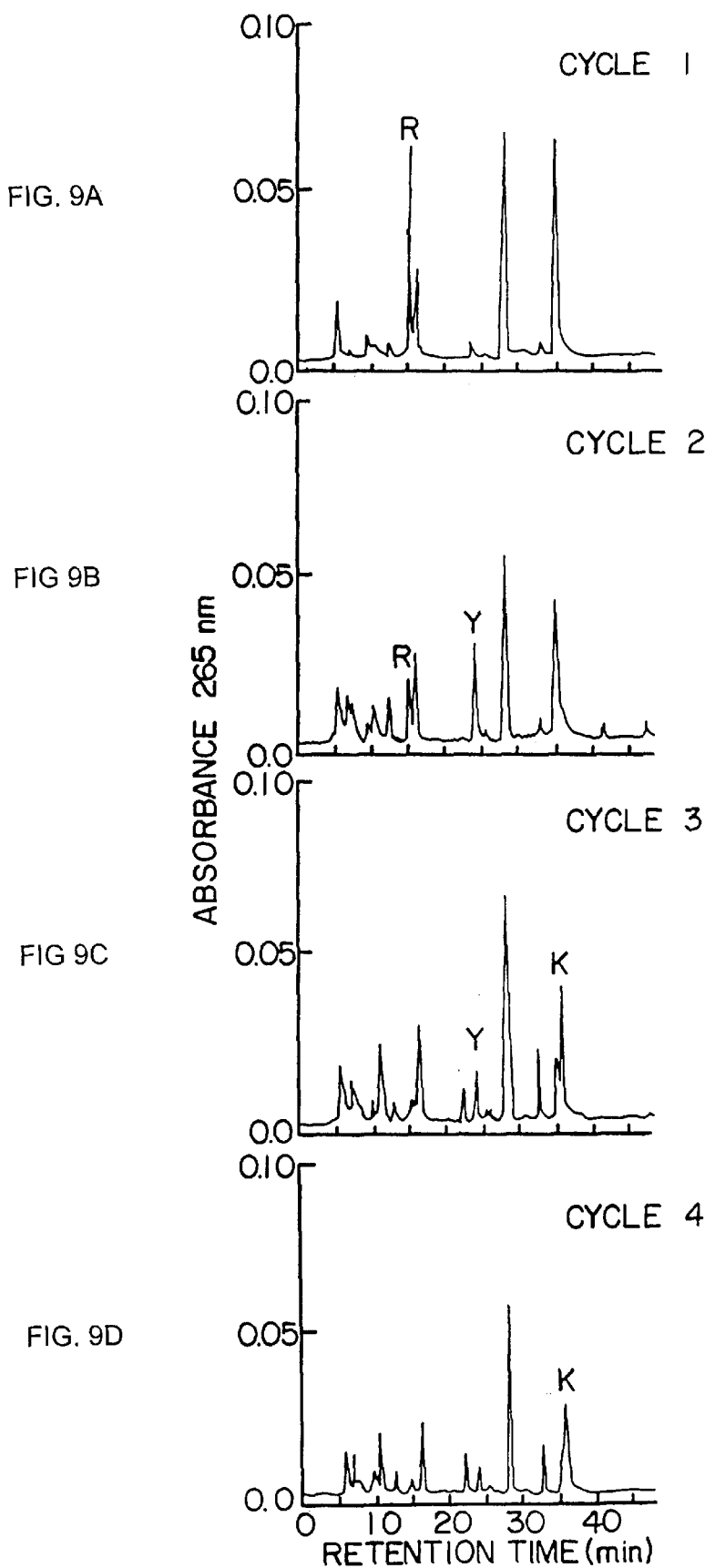
FIG. 9 illustrates the practice of the invention to sequence hemoglobin α chain non-covalently coupled to polytetrafluoroethylene (Zitex).

Column 2,
Line 1, delete "FIG. 7 illustrates" insert --FIGS. 7A-7D illustrate--.
Line 4, delete "FIG. 8 illustrates" insert --FIGS 8A-8D illustrate--.
Line 8, delete "FIG. 9 illustrates" insert --FIGS. 9A-9D illustrate--.

Column 7,
Lines 19 and 20, delete "FIG. 2 shows" insert --FIGS. 2A-2D, respectively, show--.
Line 35, delete "FIG. 3" insert --FIGS. 3A, 3B and 3C--.
Line 52, delete "are depicted by FIG. 5" insert --of cycles 1, 2 and 3 are depicted by FIGS. 5A, 5B, and 5C, respectively--.
Line 63, delete "are depicted by FIG. 6" insert --of cycles 1,2,3. and 4 are depicted by FIGS. 6A, 6B, 6C and 6D, respectively--.

In the Abstract
In the abstract "occuring" should be --occurring--.

In the Specification:
Column 8,
Lines 7 and 8, delete "are depicted by FIG. 7" insert --of cycles 1,2,3, and 4 are depicted by FIGS. 7A, 7B, 7C and 7D, respectively.--.
Line 18, delete "are depicted by FIG. 8" insert --of cycles 1,2,3, and 4 are depicted by FIGS. 8A, 8B, 8C and 8D, respectively--

UNITED STATES PATENT AND TRADEMARK OFFICE
CERTIFICATE OF CORRECTION

PATENT NO. : 5,998,213
DATED : December 7, 1999
INVENTOR(S) : Bailey et al.

It is certified that error appears in the above-identified patent and that said Letters Patent is hereby corrected as shown below:

<u>Column 8, contd.</u>
Line 28, delete "are depicted by FIG. 9" insert --of cycles 1,2,3, and 4 are depicted by FIGS. 9A, 9B, 9C and 9D, respectively--.
Line 32, delete "examples" insert --example--.

Signed and Sealed this

Nineteenth Day of June, 2001

*Attest:*

*Attesting Officer*

NICHOLAS P. GODICI
*Acting Director of the United States Patent and Trademark Office*